US006720480B2

(12) United States Patent
Crane et al.

(10) Patent No.: US 6,720,480 B2
(45) Date of Patent: Apr. 13, 2004

(54) MAIZE PROTEINASE INHIBITOR-LIKE POLYNUCLEOTIDES AND DEFENSE-ACTIVATED PROMOTER, TRANSFORMED PLANTS, AND METHODS OF USE

(75) Inventors: Virginia C. Crane, Des Moines, IA (US); Carl R. Simmons, Des Moines, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 51 days.

(21) Appl. No.: 10/039,836

(22) Filed: Oct. 23, 2001

(65) Prior Publication Data

US 2003/0033632 A1 Feb. 13, 2003

Related U.S. Application Data

(60) Provisional application No. 60/243,167, filed on Oct. 25, 2000.

(51) Int. Cl.$^7$ .............................. A01H 5/00; A01H 5/10; C12N 15/82; C12N 15/11
(52) U.S. Cl. .................... 800/298; 800/278; 435/320.1; 435/419; 536/24.1
(58) Field of Search .............................. 435/320.1, 419, 435/468; 800/298, 278; 536/24.1

(56) References Cited

U.S. PATENT DOCUMENTS 6,462,257 B1 * 10/2002 Perera et al. ............... 800/287

OTHER PUBLICATIONS

Maiti et al, 1997, Transgen. Res., 6:143–156).*
Doelling et al, 1995, Plant J. 8:683–692).*
Donald et al, 1990, EMBO J. 9:1717–1726.*
Chen et al, 2000, Sex. Plant Reprod. 13:85–94.*
Benfrey et al, 1990, Science 250:959–966.*
Kim et al,1994, Plant Mol. Biol. 24:105–117.*

* cited by examiner

Primary Examiner—Amy J. Nelson
Assistant Examiner—Anne Kubelik
(74) Attorney, Agent, or Firm—Pioneer Hi-Bred International, Inc.

(57) ABSTRACT

Methods and compositions for modulating development and defense response are provided. Nucleotide sequences encoding a maize proteinase inhibitor-like protein is provided. Nucleotide sequences comprising the proteinase inhibitor-like promoter are also provided. Methods of using the promoter to express nucleic acid sequences of interest are provided. The sequences can be used in expression cassettes for modulating development, developmental pathways, and the plant defense response. Plants, plant cells, tissues, and seed transformed with the proteinase inhibitor-like gene or its promoter are also provided.

7 Claims, No Drawings

MAIZE PROTEINASE INHIBITOR-LIKE POLYNUCLEOTIDES AND DEFENSE-ACTIVATED PROMOTER, TRANSFORMED PLANTS, AND METHODS OF USE

CROSS REFERENCE TO RELATED APPLICATION

This application claims the benefit of U.S. Provisional Application No. 60/243,167 filed Oct. 25, 2000, which is hereby incorporated by reference in its entirety.

FIELD OF THE INVENTION

The invention relates to the field of the genetic manipulation of plants, particularly the modulation of gene activity and development in plants and increased disease resistance.

BACKGROUND OF THE INVENTION

Disease in plants is caused by biotic and abiotic causes. Biotic causes include fungi, viruses, bacteria, and nematodes. An example of the importance of plant disease is illustrated by phytopathogenic fungi, which cause significant annual crop yield losses as well as devastating epidemics. Plant disease outbreaks have resulted in catastrophic crop failures that have triggered famines and caused major social change. Pathogenic fungi attack all of the approximately 300,000 species of flowering plants, however, a single plant species can be host to only a few fungal species, and similarly, most fungi usually have a limited host range. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Molecular methods of crop protection have the potential to implement novel mechanisms for disease resistance and can also be implemented more quickly than traditional breeding methods. Accordingly, molecular methods are needed to supplement traditional breeding methods to protect plants from pathogen attack.

A host of cellular processes enable plants to defend themselves against disease caused by pathogenic agents. These defense mechanisms are activated by initial pathogen infection in a process known as elicitation. In elicitation, the host plant recognizes a pathogen-derived compound known as an elicitor; the plant then activates disease gene expression to limit further spread of the invading microorganism. It is generally believed that to overcome these plant defense mechanisms, plant pathogens must find a way to suppress elicitation as well as to overcome more physically-based barriers to infection, such as reinforcement and/or rearrangement of the actin filament networks near the cell's plasma membrane.

Thus, the present invention solves needs for enhancement of the plant's defensive elicitation response via a molecularly based mechanism which can be quickly incorporated into commercial crops.

SUMMARY OF THE INVENTION

Nucleic acids and proteins relating to plant disease resistance are provided. In particular, proteinase inhibitor-like nucleic acid and protein sequences and a nucleotide sequence comprising an inducible promoter are provided. The nucleic acid sequences can be used to alter the level, tissue, or timing of expression of the plant genes to achieve enhanced disease resistance. Transgenic plants comprising the nucleic acids of the present invention are also provided. Methods for modulating the expression of the nucleic acids in a transgenic plant are additionally disclosed.

Therefore, in one aspect, the present invention relates to an isolated nucleic acid comprising (a) a polynucleotide encoding proteinase inhibitor-like polypeptides of the present invention; (b) a polynucleotide comprising at least 20 contiguous bases of the polynucleotides of the present invention; (c) a polynucleotide having at least 60% sequence identity to the polynucleotides of the present invention; and (d) a polynucleotide complementary to a polynucleotide of (a) through (c). The isolated nucleic acid can be DNA. The isolated nucleic acid can also be RNA.

In another aspect, the present invention relates to vectors comprising the polynucleotides of the present invention. Also, the present invention relates to recombinant expression cassettes, comprising a nucleic acid of the present invention operably linked to a promoter. In addition, the present invention relates to recombinant expression cassettes.

In another aspect, the present invention is directed to a host cell having stably incorporated the the recombinant expression cassette.

In yet another aspect, the present invention relates to a transgenic plant or plant cell comprising a recombinant expression cassette with a promoter operably linked to any of the isolated nucleic acids of the present invention. Preferred plants containing the recombinant expression cassette of the present invention include but are not limited to maize, soybean, sunflower, sorghum, canola, wheat, alfalfa, cotton, rice barley, and millet. The present invention also provides transgenic seed from the transgenic plant.

In another aspect, the present invention relates to an isolated protein comprising (a) a proteinase inhibitor-like polypeptide; (b) a polypeptide comprising at least 20 contiguous amino acids of SEQ ID NO: 2; (c) a polypeptide comprising at least 60% sequence identity to SEQ ID NO: 2; (d) a polypeptide encoded by a nucleic acid of the present invention; (e) a polypeptide characterized by SEQ ID NO: 2; and (f) a conservatively modified variant of SEQ ID NO: 2.

In a further aspect, the present invention relates to a method of modulating the level of protein in a plant by introducing into a plant cell a recombinant expression cassette comprising a polynucleotide of the present invention operably linked to a promoter; culturing the plant cell under plant growing conditions to produce a regenerated plant; and inducing expression of the polynucleotide for a time sufficient to modulate the protein of the present invention in the plant. Preferred plants of the present invention include but are not limited to maize, soybean, sunflower, sorghum, canola, wheat, alfalfa, cotton, rice, barley, and millet. The level of protein in the plant can either be increased or decreased.

In another aspect, the present invention further relates to recombinant expression cassettes, comprising an inducible promoter of the present invention operably linked to a nucleotide sequence of interest. In addition, the present invention relates to the recombinant expression cassettes comprising such DNA constructs.

In further aspect, the present invention relates to a method of modulating the level of a nucleotide sequence of interest in a plant by introducing into a plant cell a recombinant expression cassette comprising a nucleotide sequence of interest operably linked to the proteinase inhibitor-like promoter of the invention; and culturing the plant cell under plant growing conditions to produce a regenerated plant.

Exposure of the transformed plant to a stimulus regulates transcription of the nucleotide sequence of interest. Preferred plants of the present invention include but are not limited to maize, soybean, sunflower, sorghum, canola, wheat, alfalfa, cotton, rice, barley, and millet.

DETAILED DESCRIPTION OF THE INVENTION

Compositions of the invention comprise a proteinase inhibitor-like sequence. In particular, the present invention provides for isolated nucleic acid molecules comprising nucleotide sequences encoding the amino acid sequence shown in SEQ ID NO: 2. Further provided are polypeptides having an amino acid sequence encoded by a nucleic acid molecule described herein, for example those set forth in SEQ ID NO:1 and fragments and variants thereof.

The present invention provides a novel proteinase inhibitor-like sequence. Proteinase inhibitor-like sequences have antifungal and antimicrobial activity. Plant seeds contain a large number of protease inhibitors of animal, fungal, and bacterial origin. Other plant tissues also express proteinase inhibitors. Members of both the Bowmann-Birk and the double-headed proteinase inhibitor family have been shown to be induced in response to wounding, and hence have been implicated in the plant defense response. Thus, increased expression of the genes that encode the proteinase inhibitor-like proteins of the present invention find use in enhancing disease resistance of plants. It is further recognized that the decreased expression of the sequences of the invention may lead to nutrient enhancement.

By "disease resistance" is intended that the plants avoid the disease symptoms that are the outcome various abiotic and/or biotic stresses. That is, the plant diseases and/or the associated disease symptoms caused by the various stimuli are minimized or lessened. As such, a polypeptide or a nucleic acid sequence that enhances disease resistance minimizes the physiological consequences of biotic and/or abiotic stresses which lead to plant disease. Of particular interest is minimizing or lessening the plant disease and the associated disease symptoms resulting from a response to an external stimulus, such as a pathogens, wounding, or environmental stresses, including but not limited to, drought, temperature, and salinity.

Furthermore, present invention provides compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants. Thus, the present invention provides utility in such exemplary applications as enhanced disease resistance in plants.

The present invention further provides a defense-inducible promoter sequence. In particular, the present invention provides for an isolated nucleic acid molecule comprising the nucleotide sequence shown in SEQ ID NO:3.

By "defense-inducible" is intended that transcription of nucleotide sequences operably linked to the defense-inducible promoter is regulated when the plant is exposed to biotic and abiotic stress. By "regulate" is intended the repression or activation of transcription from a promoter region. The regulation of transcription by the promoter sequences of the present invention is defined herein as "inducible." By "inducible" is intended the ability of the promoter sequence to regulate expression of an operably linked nucleotide sequence in response to a stimulus.

By "stimulus" is intended an elemental or molecular species which either directly or indirectly regulates the activity (i.e., an increase in initiation or expression) of an inducible promoter. By "direct action" is intended that the stimulus regulates transcription via a direct interaction between the stimulus and the DNA sequence. By "indirect action" is meant that the regulation occurs via an interaction between the stimulus and some other endogenous or exogenous component in the system, the ultimate result of the indirect action being regulation of the inducible promoter. The stimulus can result from a biotic or abiotic stress, including for example, tissue wounding (i.e., insect herbivory, wind, intentional abiotic induction of tissue injury or wounding for the purpose of experimentation and/or expression analysis); wound-responsive chemicals (i.e., chemicals that result in the activation of wound-response signal transduction pathways, including, various hormones, jasmonic acid, abscissic acid, linolenic acid, ethylene, their chemical analogues, derivatives, precursors, and the like); pathogens (i.e, fungi, bacteria, nematodes, mycoplasmas, viruses, and insects and the like); and various environmental stresses (i.e., heat, drought, cold, reactive oxygen species and/or radiation). Hence, the promoter of the present invention can be used in combination with a nucleotide sequence that enhances disease resistance, and the compositions therefor find use in the defense of a plant against disease, pathogens, and the like.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and polypeptides encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence affect the plant disease defense response by retaining proteinase inhibitor-like activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a proteinase inhibitor-like nucleotide sequence that encodes a biologically active portion of a proteinase inhibitor-like protein of the invention will encode at least 12, 25, 30, 50, 60, 70, 80, 90, 95 contiguous amino acids, or up to the total number of amino acids present in a full-length proteinase inhibitor-like protein of the invention (for example, 97 amino acids for SEQ ID NO:2).

Fragments of a proteinase inhibitor-like nucleotide sequence that is useful as a hybridization probe or PCR primer generally need not encode a biologically active portion of a proteinase inhibitor-like protein. Thus, a fragment of a proteinase inhibitor-like nucleotide sequence may encode a biologically active portion of a proteinase inhibitor-like protein, or it may be a fragment that can be used as a hybridization probe or PCR primer using methods disclosed below. A biologically active portion of a proteinase inhibitor-like protein can be prepared by isolating a portion of one of the proteinase inhibitor-like nucleotide sequences of the invention, expressing the encoded portion of the proteinase inhibitor-like protein (e.g., by recombinant expression in vitro), and assessing the activity of the encoded portion of the proteinase inhibitor-like protein (i.e., enhanced disease resistance). Nucleic acid molecules that are fragments of a proteinase inhibitor-like nucleotide sequence comprise at least 16, 20, 50, 75, 100, 150, 200, 250, 300, 350, 400, 450, 470 nucleotides, or up to the number of nucleotides present in a full-length proteinase inhibitor like nucleotide sequence disclosed herein (for example, 472 nucleotides for SEQ ID NO: 1).

By "variants" is intended substantially similar sequences. For nucleotide sequences, conservative variants include those sequences that, because of the degeneracy of the genetic code, encode the amino acid sequence of one of the polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a proteinase inhibitor-like protein of the invention. Generally, variants of a particular nucleotide sequence of the invention will have at least 60%, 70%, generally at least 75%, 80%, 85%, 90%, 91%, 92%, 93%, 94%, 95%, 96%, 97%, 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active that is they continue to possess the desired biological activity of the native protein, hence they will continue to possess proteinase inhibitor-like activity. Such variants may result from, for example, genetic polymorphism or from human manipulation. Biologically active variants of a proteinase inhibitor-like native protein of the invention will have at least 60%, 70%, generally at least 75%, 80%, 85%, 90%, 91%, 92%, 93%, 94%, 95%, 96%, 97%, 98%, 99% more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the proteinase inhibitor-like proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired proteinase inhibitor-like activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by either an enhanced resistance to pathogens or a modulation in a plant developmental process when expression of the protein sequence is altered.

Variant nucleotide sequences and proteins also encompass sequences and proteins derived from a mutagenic and recombinogenic procedure such as DNA shuffling. With such a procedure, one or more different proteinase inhibitor-like coding sequences can be manipulated to create a new proteinase inhibitor-like possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the proteinase inhibitor-like gene of the invention and other known proteinase inhibitor-like genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al.

(1998) *Nature* 391:288–291; and U.S. Pat. Nos. 5,605,793 and 5,837,458.

The compositions of the invention also include isolated nucleic acid molecules comprising the promoter nucleotide sequence set forth in SEQ ID NO:3. By "promoter" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate.

It is recognized that having identified the nucleotide sequences for the promoter regions disclosed herein, it is within the state of the art to isolate and identify additional regulatory element in the 5' untranslated region upstream from the particular promoter regions defined herein. Thus for example, the promoter regions disclosed herein may further comprise upstream regulatory elements that confer tissue-preferred expression of heterologous nucleotide sequences operably linked to the disclosed promoter sequence. See particularly, Australian Patent No. AU-A-77751/94 and U.S. Pat. Nos. 5,466,785 and 5,635,618.

Fragments and variants of the disclosed proteinase inhibitor-like promoter nucleotide sequence are also encompassed by the present invention. By "fragment" is intended a portion of the nucleotide sequence. Fragments of a nucleotide sequence may retain biological activity and hence retain their transcriptional regulatory activity. Thus, for example, less than the entire promoter sequence disclosed herein may be utilized to drive expression of an operably linked nucleotide sequence of interest, such as a nucleotide sequence encoding a heterologous protein. Alternatively, fragments of a nucleotide sequence that are useful as hybridization probes generally do not retain biological activity. Thus, fragments of a nucleotide sequence may range from at least about 20 nucleotides, about 50 nucleotides, about 100 nucleotides, and up to the full-length nucleotide sequence of the invention.

Thus, a fragment of a proteinase inhibitor-like promoter nucleotide sequence may encode a biologically active portion of the proteinase inhibitor-like promoter, CI it may be a fragment that can be used as a hybridization probe or PCR primer using methods disclosed below. A biologically active portion of a proteinase inhibitor-like promoter can be prepared by isolating a portion of one of the proteinase inhibitor-like promoter nucleotide sequences of the invention, and assessing the activity of the portion of the proteinase inhibitor-like promoter. Nucleic acid molecules that are fragments of a proteinase inhibitor-like promoter nucleotide sequence comprise at least 16, 20, 50, 75, 100, 150, 200, 250, 300, 350, 400, 450, 500, 550, 600, 650, 700, 800, 850, 900 nucleotides, or up to the number of nucleotides present in a full-length proteinase inhibitor-like promoter nucleotide sequence disclosed herein (for example, 925 nucleotide for SEQ ID NO: 3). Assays to determine the activity of a promoter sequence are well known in the art. For example, a proteinase inhibitor-like promoter fragment or variant may be operably linked to the nucleotide sequence encoding any report protein, such as the β-glucuronidase protein (GUS reporter) or the luciferase protein. The DNA construct is inserted into the genome of a plant or plant cell and the mRNA or protein levels of the reporter sequence is determined. See, for example, Eulgem et al. (1999) *EMBO Journal* 18: 4689–4699.

The nucleotide sequences of the invention can be used to isolate corresponding sequences from other organisms, particularly other plants, and more particularly other monocots. In this manner, methods such as PCR, hybridization, and the like can be used to identify such sequences based on their sequence homology to the sequences set forth herein. Sequences isolated based on their sequence identity to the entire proteinase inhibitor-like polynucleotides and promoter sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the proteinase inhibitor-like polynucleotides and promoter sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire sequence disclosed herein, or one or more portions thereof, may be used as a probe capable of specifically hybridizing to corresponding disease resistant sequences and messenger RNAs. To achieve specific hybridization under a variety of conditions, such probes include sequences that are unique among disease resistant sequences and are preferably at least about 10 nucleotides in length, and most preferably at least about 20 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the $T_m$ can be approximated from the equation of Meinkoth and Wahl (1984) *Anal. Biochem.* 138:267–284: $T_m=81.5°$ C.+16.6 (log M)+0.41 (%GC)−0.61 (% form)−500/L; where M is the morality of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point $(T_m)$ for the specific sequence and its complement at a defined ionic strength and pH. However, severely stringent conditions can utilize a hybridization and/or wash at 1, 2, 3, or 4° C. lower than the thermal melting point $(T_m)$; moderately stringent conditions can utilize a hybridization and/or wash at 6, 7, 8, 9, or 10° C. lower than the thermal melting point $(T_m)$; low stringency conditions can utilize a hybridization and/or wash at 11, 12, 13, 14, 15, or 20° C. lower than the thermal melting point $(T_m)$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier. N.Y.); and Ausubel et al., eds. (1995) *Current Protocols in Molecular Biology*, Chapter 2 (Greene Publishing and Wiley-Interscience, New York). Sec Sambrook et al. (1989) *Molecular Cloning: A Laboratory Manual* (2d ed., Cold Spring Harbor Laboratory Press, Plainview. N.Y.).

In general, sequences that have promoter activity or encode a proteinase inhibitor-like protein will be at least about 60% homologous, about 70% homologous or at least 80%, 85%, 90%, 91%, 95%, 96%, 97%, 98%, 99% or more with the disclosed sequences. That is, the sequence identity of the sequences may from about 60% to 70%, and even at least 80%, 85%, 90%, 91%, 92%, 93%, 94%, 95%, 96%, 97%, 98%, 99% or more.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nib.gov. Alignment may also be performed manually by inspection.

For purposes of the present invention, comparison of nucleotide or protein sequences for determination of percent sequence identity to the proteinase inhibitor-like sequences disclosed herein is preferably made using the ClustalW program (Version 1.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, 91%, 92%, 93%, 94%, 95%, 96%, 97%, 98%, 99% or more.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Expression of Sequences

The nucleic acid sequences of the present invention can be expressed in a host cell such as bacteria, yeast, insect, mammalian, or preferably plant cells. It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species, or, if from the same species, is substantially modified from its original form by deliberate human intervention.

By "host cell" is meant a cell, which comprises a heterologous nucleic acid sequence of the invention. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The sequences of the invention are provided in expression cassettes or DNA constructs for expression in the plant of interest. The cassette will include 5' and 3' regulatory sequences operably linked to a proteinase inhibitor-like sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the disease resistant sequence to be under the transcriptional regulation of the regulatory regions. The expression cassette may additionally contain selectable marker genes.

The expression cassette will include in the 5'-3' direction of transcription, a transcriptional and translational initiation region, a proteinase inhibitor-like DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of the disease resistant RNA/protein in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.*

6:2419–2422; Barkley et al. (1980) in *The Operon*, pp. 177–220; Hu et. al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambrotti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in plants. Such constitutive promoters include, for example, the core promoter of the Rsyn7 (WO 99/43838 and U.S. Pat. No. 6,072,050); Scp1 promoter (U.S. patent application Ser. No. 09/028819), rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also Publication No. WO 99/43819, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2—2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Tissue-preferred promoters can be utilized to target enhanced the expression of the proteinase inhibitor-like sequences within a particular plant tissue. Tissue-preferred promoters include Yamamoto et al. (1997) *Plant J.* 12(2) :255–265; Kawamata et al. (1997) *Plant Cell Physiol.* 38(7) :792–803; Hansen et al. (1997) *Mol. Gen Genet.* 254(3) :337–343; Russell et al. (1997) *Transgenic Res.* 6(2) :157–168; Rinehart et al. (1996) *Plant Physiol.* 112(3) :1331–1341; Van Camp et al. (1996) *Plant Physiol.* 112(2) :525–535; Canevascini et al. (1996) *Plant Physiol.* 112(2) :513–524; Yamamoto et al. (1994) *Plant Cell Physiol.* 35(5) :773–778; Lam (1994) *Results Probl. Cell Differ.* 20:181–196; Orozco et al. (1993) *Plant Mol Biol.* 23(6): 1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

Additional tissue-preferred promoters include silk preferred, endosperm-preferred, and pericarp-preferred promoters. Examples of such promoters are known in the art. See, for example, Digeon et al. (1999) *Plant Molecular Biology* 39:1101–1112 and Sidorenko et al. (2000) *Plant Journal* 22:471–482, both of which are incorporated herein by reference.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Nat. Acad. Sci. USA* 83:5602–5606, Agrobacterium-mediated transformation (Townsend et al., U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926); and Lec1 transformation (WO 00/28058). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved. One of skill will recognize that after the recombinant expression cassette is stably incorporated in transgenic plants and confirmed to be operable, it can be introduced into other plants by sexual crossing. Any of number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plans that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Backcrossing to a parental plant and out-crossing with a non-transgenic plant are also contemplated.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (*Tulipa* spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, maize, Brassica, soybean, cotton, safflower, peanut, sorghum, wheat, millet, tobacco, etc.), more preferably corn and soybean plants, yet more preferably corn plants.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva et al. (1983) *Gene* 22:229–235); Mosbach et al. (1983) *Nature* 302:543–545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous nucleotide sequences in yeast is well known. Sherman, F., et al. (1982) *Methods in Yeast Genetics*, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lists. The monitoring of the purification process can be accomplished by using Western blot techniques or radioimmunoassay of other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49). and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosgphila cell lines such as a Schneider cell line (See, Schneider, J. *Embryol. Exp. Morphol.* 27:353–365 (1987).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al.(1983) *J. Virol.* 45:773–781). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213–238(1985).

Animal and lower cukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells arc cultured by means well known in the art. Kuehler, R. J., *Biochemical Methods In Cell Culture and Virology*. Dowden, Hutchinson and Ross, Inc (1997).

It is recognized that with these nucleotide sequences, antisense constructions, complementary to at least a portion of the messenger RNA (mRNA) for the proteinase inhibitor-like sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The present invention further provides a method for modulating (i.e., increasing or decreasing) the concentration or composition of the sequences of the present invention in a plant or part thereof. Increasing or decreasing the concentration and/or the composition (i.e., the ratio of the polypeptides of the present invention) in a plant can effect modulation. The method comprises introducing into a plant cell, a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or composition in the plant or plant part.

In some embodiments, the content and/or composition of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

In general, concentration or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds, which activate expression from these promoters, are well known in the art. In preferred embodiments, the polypeptides of the present invention are modulated in monocots, particularly maize.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731, 181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774–8778; herein incorporated by reference.

Disease and Pests

The proteinase inhibitor-like sequences of the present invention are involved in cellular functions that modulate the plant defense response. Hence, the sequences of the invention may find use in disrupting cellular function of plant pathogens or insect pests as well as altering the defense mechanisms of a host plant to enhance resistance to disease. Accordingly, the compositions and methods are also useful in protecting plants against pathogens, including for example, fungal pathogens, viruses, nematodes, insects and the like.

By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267: 2228–2233, both of which are herein incorporated by reference).

Methods for increasing pathogen resistance in a plant are provided. The methods involve stably transforming a plant with a DNA construct comprising an anti-pathogenic nucleotide sequence of the invention operably linked to promoter that drives expression in a plant. Such methods may find use in agriculture particularly in limiting the impact of plant pathogens of crop plants. The anti-pathogenic nucleotide sequences comprise the proteinase inhibitor-like nucleic acid molecules. While the choice of promoter will depend on the desired timing and location of expression of the anti-pathogenic nucleotide sequences, preferred promoters include constitutive and pathogen-inducible promoters.

Additionally, the compositions can be used in formulation use for their disease resistance activities. The proteins of the invention can be formulated with an acceptable carrier into a pesticidal composition(s) that is for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Additionally, transformed plants, plant cells, plant tissues and seeds thereof are provided.

It is recognized that the present invention is not dependent upon a particular mechanism of defense. Rather, the genes and methods of the invention work to increase resistance of the plant to pathogens independent of how that resistance is increased or achieved.

The methods of the invention can be used with other methods available in the art for enhancing disease resistance in plants. Similarly, the plant defense mechanisms described herein may be used alone or in combination with other proteins or agents to protect against plant diseases and pathogens. Other plant defense proteins include those described in copending applications entitled "*Methods for Enhancing Disease Resistance in Plants*", U.S. Application Serial No. 60/076,151, filed Feb. 26, 1998, and U.S. Application Serial No. 60/092,464, filed Jul. 11, 1998, and copending application entitled "*Genes for Activation of plant Pathogen Defense Systems*", U.S. Application Serial No. 60/076,083, filed Feb. 26, 1998, all of which are herein incorporated by reference.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* f.sp. glycinea, *Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Coiletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum,* Phialophora gregata, Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium* splendens, *Pythium debaryanum, Pythium aphanidermatum, Phytophthora megasperma, Peronospora trifoliorum, Phoma medicaginis var. medicaginis, Cercospora medicaginis, Pseudopeziza medicaginis, Leptotrochila medicaginis, Fusarium, Xanthomonas campestris p.v. alfalfae, Aphanomyces euteiches, Stemphylium herbarum, Stemphylium alfalfae*; Wheat: *Pseudomonas syringae p.v. atrofaciens, Urocystis agropyri, Xanthomonas campestris p.v. translucens, Pseudomonas syringae p.v. syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis f.sp. tritici, Puccinia graminis f.sp. tritici, Puccinia recondita f.sp. tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis var. tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Orobanche, Plasmophora halstedii, Sclerotinia sclerotiorum*, Aster Yellows, *Septoria helianthi, Phomopsis helianthi, Alternaria helianthi, Alternaria zinriae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum pv. carotovora, Cephalosporium acremonium, Phytophthora cryptogea, Albugo tragopogonis*; Corn: *Fusarium moniliforme var. subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis O, T (Cochliobolus heterostrophus), Helminthosporium carbonum I, II & III (Cochliobolus carbonum), Exserohilum turcicum I, II & III, Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense subsp. nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi pv. zea, Erwinia carotovora*, Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae p.v. syringae, Xanthomonas campestris p.v. holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilanum (Sphacelothea reiliana), Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, lesion, and renniform nematodes, etc.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Mer-*

*omyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentials*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis epsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

In one embodiment, the sequences of the present invention are expressed in a plant and modulate the plant's resistance to ear mold. In this embodiment, the sequence of invention can be expressed in silks or husks to help reduce the sensitivity of the plant to ear molds. The proteinase inhibitor-like sequences of the invention can be used for any application including coating surfaces to target microbes. In this manner, the target microbes include human pathogens or microorganisms. Surfaces that might be coated with the proteinase inhibitor-like polypeptides of the invention include carpets and sterile medical facilities. Polymer bound polypeptides of the invention may be used to coat surfaces. Methods for incorporating compositions with antimicrobial properties into polymers are known in the art. See, U.S. Pat. No. 5,847,047, herein incorporated by reference.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in plants (ed. Andrew H. Paterson) by Academic Press/R.G. Lands Company, Austin, Tx., pp. 7–21.

The particular method of genotyping in the present invention may employ any number of molecular marker analytic techniques such as, but not limited to, restriction fragment length polymorphism's (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. in preferred embodiments, the probes are selected from polynucleotides of the present invention. Typically, these probes are cDNA probes or restriction enzyme treated (e.g., PST I) genomic clones. The length of the probes is discussed in greater detail, supra, but is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in haploid chromosome compliment. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2)denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample, preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

Methods of use for Proteinase Inhibitor-Like Promoter Sequences

The nucleotide sequences for the proteinase inhibitor-like promoters disclosed in the present invention, as well as variants and fragments thereof, are useful in the genetic manipulation of any plant or plant cell when assembled with a DNA construct such that the promoter sequence is operably linked to a nucleotide sequence encoding a heterologous nucleotide sequence of interest. In this manner, the nucleotide sequences of the proteinase inhibitor-like promoter of the invention are provided in expression cassettes along with heterologous nucleotide sequences for expression in the plant of interest.

The promoter for the proteinase inhibitor-like gene may regulate expression of operably linked nucleotide sequences in an inducible manner. That is, expression of the operably linked nucleotide sequences in a plant cell is induced in response to a stimulus. By "stimulus" is intended a chemical, which may be applied externally or may accumulate in response to another external stimulus. A stimulus includes, for example, a pathogen, which may, for example, induce expression as a result of invading a plant cell; wounding or other factor such as environmental stresses, including but not limited to, drought, temperature, and salinity. Hence, the proteinase inhibitor-like promoter sequences when operably linked to a disease resistance sequence can enhance disease resistance in a transformed plant.

Synthetic hybrid promoter regions are known it the art. Such regions comprise upstream promoter elements of one nucleotide sequence operably linked to the promoter element of another nucleotide sequence. In an embodiment of the invention, heterologous gene expression is controlled by a synthetic hybrid promoter comprising the proteinase inhibitor-like promoter sequences of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton et al. (1998) *Curr. Opin. Plant Biol.* 1:311–315. Alternatively, a synthetic proteinase inhibitor-like promoter sequence may comprise duplications of the upstream promoter elements found within the proteinase inhibitor-like promoter sequence.

It is recognized that the promoter sequence of the invention may be used with its native proteinase inhibitor-like coding sequences. A DNA construct comprising the proteinase inhibitor-like promoter operably linked with its native proteinase inhibitor-like gene may be used to transform any plant of interest to bring about a desired phenotypic change, such as enhanced disease resistance. Where the promoter and its native gene is naturally occurring within the plant, i.e., in maize, transformation of the plant with these operably linked sequences also results in either a change in phenotype, such as enhanced disease resistance or the insertion of operably linked sequences within a different region of the chromosome thereby altering the plant's genome.

In another embodiment of the invention, expression cassettes will comprise a transcriptional initiation region comprising the proteinase inhibitor-like promoter sequences disclosed herein, or variants or fragments thereof, operably linked to the heterologous nucleotide sequence. Hence, the promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, and the like. Phenotypes that alter the disease resistance of the plant to various abiotic and biotic stresses including pathogens, wounding, and environment stress are of particular interest. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. No. 08/838,763, filed Apr. 10, 1997; Ser. No. 08/824,379, filed Mar. 26, 1997; Ser. No. 08/824,382, filed Mar. 26, 1997; and U.S. Pat. No. 5,703,049; herein incorporated by reference. Another example is lysine and/or sulfur rich seed protein encoded by the soybean 2S albumin described in U.S. application Ser. No. 08/618,911, filed Mar. 20, 1996, and the chymotrypsin inhibitor from barley, described in Williamson et al. (1987) *Eur. J. Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,632, filed Nov. 1, 1996, and PCT/US97/20441, filed Oct. 31, 1997, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. application Ser. No. 08/484,815, filed Jun. 7, 1995); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins, described in U.S. application Ser. No. 08/838,763 (filed Apr. 10, 1997), Ser. No. 08/824,379 (filed Mar. 26, 1997), and Ser. No. 08/824,382 (filed Mar. 26, 1997), and U.S. Pat. No. 5,703,049, provide descriptions of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837–5847) facilitate expression of polyhyroxyalkanoce (PHAs). Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The following examples are offered by way of illustration and not by way of limitation.

EXPERIMENTAL

Example 1 mRNA Profiling

The proteinase inhibitor-like sequence of the present invention was identified by virtue of the induction of its mRNA in the ERE-avrRxv callus system which activates the maize pathogen defense system. The mRNA profiling was done using the Affymetrix technology. This technology and the results are described and shown below. The data demonstrates that the sequences of the present invention are induced in the ERE-avrRxv system, and that co-induced with them are other known defense related genes. This clearly indicates that their induction is also defense-related.

Materials and Methods

Construction of ERE-avrRxv Vector

The stable transformation experiments to create estradiol-inducible avrRxv expression used a single plasmid construct called "ERE-avrRxv". This plasmid contains three tandem plant gene expression units; the estrogen receptor, the estrogen response elements controlling avrRxv, and the selectable marker PAT (phosphinothricin acetyltransferase). For the first unit, the nos promoter region (bases 259 to 567 from Bevan et al. (1983) *Nucleic Acids Res.* 11:369–385) was cloned upstream of the 79 bp tobacco mosaic virus leader omega prime (Gallie et al. (1987) *Nucleic Acids Res.* 15:3257–3273) and the first intron of maize alcohol dehydrogenase ADH1-S (Dennis et al. (1984) *Nucleic Acids Res.* 12:3983–3990). The coding region for the human estrogen receptor (Tora et al. (1989) *EMBO Journal* 8:1981–1986) was inserted between the upstream sequences and the pinII terminator. The second unit consists of four pairs of estrogen response element ½ sites (EREs) (Klein-Hitpab et al. (1986) *Cell* 46:1053–1061) contained on two copies of the sequence, GGCCGCTCGAGTCCAAAGTCAGGTCACAGTGACCTGATCAAAGTTGTCCAAA GTCAGGTCACAGTGACCTGATCAAAGTTGTCACG (SEQ ID NO:4) (half-sites underlined) cloned upstream of the minimal ADH1-S promoter (bases −89 to +80) and the ADH1-S first intron. The avrRxv coding sequence and pinII terminator are inserted downstream. The third unit contains the cauliflower mosaic virus 35S promoter and terminator (bases 6908–7437 and 7480–7632 from Franck et al. (1980) *Cell* 21:285–294) controlling expression of a synthetic coding sequence of phosphinothricin-N-acetyltransferase, pat (Wohlleben et al. (1988) *Gene* 70:25–37) synthesized with plant preferred codons.

Production and Estradiol Treatment of ERE-avrRxv Transgenic Callus and Cell Suspensions For transformation experiments to produce transgenic ERE-avrRxv callus, immature embryos were isolated from greenhouse-grown HiII genotype plants 8–10 days after pollination. The immature embryos were isolated, cultured and prepared for bombardment as described above for the transient expression assays. Particle bombardment transformation was done as described above for immature embryo transformation, except that the transforming DNA was the "ERE-avrRxv" construct. One day after 745 embryos were bombarded, they were transferred to a selection medium similar to the initiation medium but containing 3 mg/L active ingredient of the herbicide bialaphos® (Meiji Seika Kaisha, LTD, Yokohama, Japan). From these, 48 transformed colonies were identified between 7 and 9 weeks after bombardment and selected by rapid, healthy growth. Of these 33 were PCR positive for the avrRxv gene, among them lines 197 and 186 described herein. Cell suspensions were generated from ERE-avrRxv callus line 197 and control Hill callus by forcing calli through a 1.5 mm sieve into 250 ml baffled flasks containing 70 ml of liquid Murashige and Skoog (MS) medium with MS vitamins, 3% sucrose, 2 mg/L 2,4-D. Flasks were rotated at 140 rpm in the dark at 28° C., and transfers were performed twice weekly, with periodic selections for smaller cell aggregates, with transferred cells kept to approximately 5 ml of packed volume.

Transformed callus and cell suspensions were treated with estradiol to induced avrRxv gene expression. For callus treatment the callus tissue was gently broken up into 10–20 mg pieces and then plated on the N6 agar medium described above. Three callus lines were used: HiII::nontransformed control, HiII::ERE-avrRxv line 197 and Hill::ERE-avrRxv line 186. For the experimentals ethanyl-estradiol (Sigma, St. Louis, Mo.) was dissolved in 100% ethanol to a 10 mM concentration, and then 34.8 $\mu$l of this stock was dispersed in 4 ml of $H_2O$ for an 87 $\mu$M final concentration. For the controls 34.8 $\mu$l of 100% ethanol was added. The 4 ml of solution was spread over the agar surface of 100×25 mm plates, flooding the callus cells. The plates were dried in a sterile flow hood overnight, then covered and further incubated at 23° C. in the dark, with reapplication after 72 hours. For cell suspension cultures about 5 ml of cells in a 70 ml of liquid culture received either 70 $\mu$l of 10 mM estradiol in 100% ethanol (final concentration 10 $\mu$M estradiol and 0.1% ethanol) or ethanol only for controls. At the desired timepoints, cells were collected by centrifugation.

mRNA Abundance Profiling Using the Affymetrix GeneChip® Technology

Protocols for preparing in vitro-transcribed biotinylated cRNA probes from poly-$A^+$ mRNA for Affymetrix GeneChip® gene expression analysis were according to the manufacturer's recommendations (Affymetrix, Santa Clara, Calif.; Technical Support tel. 1–888-DNA-CHIP), which, are described in Wodicka et al. (1997) *Nature Biotechnology* 15: 1359–1367. In brief, per sample 2 $\mu$g of poly-$A^+$ mRNA, described above in mRNA isolations, was used for the first strand cDNA synthesis. This involved a T7-$(dT)_{24}$ oligonucleotide primer and reverse transcriptase SuperScript II (Gibco-BRL, Gaithersburg, Md.). The second strand synthesis involved *E. coli* DNA Polymerase I (Gibco-BRL, Gaithersburg, Md.). The double-stranded cDNA was then cleaned up using phenol/chloroform extraction and phase lock gels (5 Prime-3 Prime, Inc., Boulder, Colo.) followed by ethanol precipitation. For the in vitro transcription to produce cRNA, biotin-11-CTP and biotin-16-UTP, in addition to all four NTPs, were used with T7 transcriptase (Ambion, Austin, Tx.). The IVT product was cleaned up using Rneasy affinity resin columns (Qiagen Crasworth, Calif.). Labeled in vitro transcript (IVT) yields ranged from 62–80 $\mu$g per sample. They were stored at −80° C. until use. The IVT products were fragmented in acetate buffer (pH 8.1) at 94° C. for 35 minutes prior to chip hybridization.

The GeneChip® used in these experiments was constructed by Affymetrix using a set of 1500 maize cDNA EST sequences. In brief, the 1.28 cm×1.28 cm GeneChip® contain a high-density array of 20-mer oligonucleotides affixed to a silicon wafer. These oligonucleotides were synthesized in situ on the silicon wafer by a light-dependent combinatorial chemical synthesis (Fodor et al. (1991) *Science* 251: 767–773; Pease et al. (1994) *Proc. Natl. Acad. Sci.* 91: 5022–5026). The oligonucleotide sequences are complementary to the sense strand of Pioneer Hi-Bred's cDNA EST sequences. For each gene there are up to forty 20-mer oligonucleotides synthesized. Twenty of these oligonucleotides are exact matches to different, though sometimes overlapping, regions of the EST sequence. The other 20 oligonucleotides contain one base mismatch in the center, which changes hybridization efficiency. (For a minority of genes there were less than 20 oligo probe pairs, but never less than 15 pairs per gene). The perfect match (PM) and mismatch (MM) oligo probe pairs for each gene are tiled in adjacent regions of the GeneChip. Comparison of the hybridization intensities between different PM oligonucleotides for a given gene, and between PM to MM hybridization intensities for an oligonucleotide pair, are used to determine the overall hybridization to the gene, and hence its level of mRNA abundance in the samples (see Wodicka et al. (1997) *Nature Biotechnology* 15: 1359–1367).

Probes of in vitro labeled transcript were prepared essentially as described (Wodicka et al. (1997) *Nature Biotechnology* 15: 1359–1367) for each of the following four samples: 1) HiII callus control (not estradiol treated); 2) HiII callus estradiol treated; 3) ERE-avrRxv callus (line 197) control; and 4) ERE-avrRxv callus (line 197) estradiol treated. Twelve $\mu$g IVT for each sample were used per chip hybridization. Each sample was hybridized twice (reps A and B), each rep using a different chip. Hybridization and image scanning conditions, and quantitative analysis and intensity calculations, were essentially as described (Wodicka et al. (1997) *Nature Biotechnology* 15: 1359–1367). Comparisons of mRNA abundances were made between each rep of each sample; a total of 8 comparisons. Positive gene expression changes were defined as those showing a 2-Bio or more change in at least three of these four comparisons made between the HiII control and ERE-avrRxv genotypes. The average and standard error for expression fold changes were calculated from the values of these three or four comparisons.

Results

A high density Affymetrix GeneChip® array of some 1500 maize gene sequences was used for surveying mRNA expression changes caused by avrRxv expression in transgenic ERE-avrRxv callus. It was observed that estradiol treatment of ERE-avrRxv callus caused an average 8.7 fold change in mRNA abundance of the proteinase inhibitor-like mRNA as measured by relative fluorescent intensity of hybridizing signal. The average and SE were calculated from 3 or 4 chip comparisons.

The proteinase inhibitor-like sequences of the present invention are probable plant defense-related genes, and so these mRNA profiling results further support that a defense reaction is caused by avrRvx.

Example 2

Transient Assay for Defense Activation of the Proteinase Inhibitor-like Promoter Sequence The proteinase inhibitor-like promoter sequence of the present invention (SEQ ID NO:3) was cloned into the ECOR1 site of Invitrogen's TA vector, as a PCR product from an A63 Genome Walker (Clontech) library. This promoter sequence was operably linked to a GUS reporter gene and tested for activity in a transient assay for plant defense-induction.

The promoter sequence of SEQ ID NO:3 was found to induce expression of the operably linked nucleotide sequence under the following transient defense activation assays. The nucleotide sequences significantly increased transcription in GS3 cells at 2 h and 6 h after treatment with chito-oligosaccharides or *F. moniliforme* spores. No background expression in GS3 suspension cells was found. In addition, the nucleotide sequences significantly increased transcription induced in HT1 silks 1 hour following inoculation with *F. moniliforme* spores. The induction persisted for at least 24 h.

Furthermore, Carbonum/HCT experiments demonstrated that *C. carbonum* (tox−) spores delivered on soaked filter papers resulted in a 3.5 fold increase in expression level of nucleotide sequences operably linked to the promoter. *C. carbonum* (tox−) spores delivered by spraying to run-off increased expression levels by of the reporter sequence by 2 fold, as did application of HC-toxin (1 μg/ml). The combined application of both *C. carbonum* (tox−) and HC-toxin increased expression of reported sequences 3 fold, and the application of *C. carbonum* (tox+) increased expression of the sequences 1.5 fold. Expression levels were obtained from Northern analysis and represent an average of 3 repeated experiments.

The activity of the promoter was also studied in the presence of the putative defense activator, zmNPR1. Specifically, maize immature embryos (IE) were co-bombarded with the zmBBI1::GUS construct along with Act::luciferease as an internal standard and either a carrier DNA or an putative defense activators, zmNPR1 (U.S. patent application Ser. No. 09/551,778, filed Apr. 18, 2000, herein incorporated by reference). Particle preparation and DNA coating were carried out as described by Zhang et al.((2000) Plant Cell Reports 19:241–250) except for use of tungsten (1.0 μm) particles and different amounts of DNA: 50 μl zmBBI1::GUS at 0.02 μg/μl, Act::luciferase at 0.1 μg/μl, and 5 μl of the carrier or activator DNA at 1.0 μg/μl. The amount of DNA delivered for each bombardment were 0.33, 0.17, and 1.67 μg for zmBBI1::GUS, Act::luciferase, and the carrier or activator, respectively. The DNA concentration for zmBBI1::GUS was chosen in previous experiments for low background expression. A total of 45 IEs were used for each bombardment. IEs were placed on the osmotic medium (Vain et al. (1993) *Plant Cell Reports* 12:84–88) for 4 h before bombardment. The distance from the stopping screen to the target was 10 cm and bombardment was done at 650 psi with a PDS 1000/He device (Bio-Rad Laboratories).

After the bombardment the IEs were cultured on the same osmotic medium for 20–24 hr. Subsequently, the 45 IEs were randomly divided into three groups, 15 IEs for each. They were, then, transferred to three new petri dishes (60×25 mm) for chemical treatments. A piece of filter paper had been placed in each petri dish and wetted with 1.25 ml of 560Y liquid medium containing no chemical, 1 mM SA and 0.1 mM JA, respectively. The IEs were cultured again for another 20 h.

Three IEs from each group were then histochemically stained in X-Gluc staining solution (McCabe et al. (1988) Bio/Technology 6:923–926) for overnight at 37° C. The rest of the IEs were subjected to GUS fluorometric and luciferase assays. Fluorometric measurements of GUS activity were performed by using 50 μl protein extract prepared from the 12 IEs of each treatment and quantified in Fluoroskan Ascent FL (Labsystem) for two time points, 10 and 30 min. Luciferase activity was quantified in a Monolight 2010 (Analytical Luminescence Lab) by mixing 20 μl of protein extract with 100 μl of reaction buffer (Dual-Luciferase Reporter Assay System, Promega) and taking the measurements after 10 s. To normalized promoter activity, the GUS value detected in each sample was divided by the luciferase value obtained in the same bombarded sample treated with no chemicals.

The results of cobombardment with zmBBI1::GUS and zmNPR1 are shown in tables 1 and 2. The results demonstrate that SA induces expression of sequence operably linked to the proteinase inhibitor-like promoter sequence. Interestingly, while the proteinase inhibitor-like sequence is induced in the presence of SA, the defense regulator zmNPR1 down-regulate expression.

TABLE 1

| Rep | Construct | zmNPR1 | Chemical | GUS pmol MU/min/ml extract (ave) | | Lucif | | Lucif/adj for SA (/0.38) | GUS/Luci | Lucif/adj for SA and JA (Luci for none) | GUS/Luci |
|---|---|---|---|---|---|---|---|---|---|---|---|
| backg | | | | 45.6 | 0 | 114 | 0 | | | | |
| 1 | zmBBI1::GUS | N | none | 77.19 | 31.59 | 20230 | 20116 | 20002 | 15.79 | 20002 | 15.79 |
| | | | SA | 122.31 | 76.71 | 8587 | 8473 | 21997 | 34.87 | 20002 | 38.35 |
| | | | JA | 58.61 | 13.01 | 15131 | 15017 | 14903 | 8.73 | 20002 | 6.50 |
| | | Y | none | 61.52 | 15.92 | 30516 | 30402 | 30288 | 5.26 | 30288 | 5.26 |
| | | | SA | 106.54 | 60.94 | 16829 | 16715 | 43687 | 13.95 | 30288 | 20.12 |
| | | | JA | 55.25 | 9.65 | 28681 | 28567 | 28453 | 3.39 | 30288 | 3.19 |
| 2 | | N | none | 62.16 | 16.56 | 14343 | 14229 | 14115 | 11.73 | 14155 | 11.70 |
| | | | SA | 102.94 | 57.34 | 7223 | 7109 | 18408 | 31.15 | 14155 | 40.15 |
| | | | JA | 62.22 | 16.62 | 14782 | 14668 | 14554 | 11.42 | 14155 | 11.74 |
| | | Y | none | 60.29 | 14.69 | 28383 | 28269 | 28155 | 5.22 | 28155 | 5.22 |
| | | | SA | 99.71 | 54.11 | 14016 | 13902 | 36284 | 14.91 | 28155 | 19.22 |
| | | | JA | 54.57 | 8.97 | 25552 | 25438 | 25324 | 3.54 | 28155 | 3.19 |

TABLE 2a

| | Rep 1 | | Rep 2 | |
|---|---|---|---|---|
| | NPR1−, | NPR1+ | NPR1−, | NPR1+ |
| none | 15.79 | 5.26 | 11.7 | 5.22 |
| SA | 38.35 | 20.12 | 40.51 | 19.22 |
| JA | 6.5 | 3.19 | 11.74 | 3.19 |

TABLE 2b

| | Rep 1 | | Rep 2 | |
| --- | --- | --- | --- | --- |
| | NPR1-, | NPR1 + | NPR1-, | NPR1+ |
| none | 15.79 | 5.26 | 11.73 | 5.22 |
| SA | 34.87 | 13.95 | 31.15 | 14.91 |
| JA | 8.73 | 3.39 | 11.42 | 3.54 |

Example 3
Identification of the Gene From a Computer Homology Search

Gene identities can be determined by conducting BLAST (Basic Local Alignment Search Tool; Altschul, S. F., et al. (1993) *J. Mol. Biol.* 215:403–410; see also www.ncbi.nlm.nih.gov/BLAST/) searches under default parameters for similarity to sequences contained in the BLAST "nr" database (comprising all non-redundant Gen-Bank CDS translations, sequences derived from the 3-dimensional structure Brookhaven Protein Data Bank, the last major release of the SWISS-PROT protein sequence database, EMBL, and DDBJ databases). The cDNA sequences are analyzed for similarity to all publicly available DNA sequences contained in the "nr" database using the BLASTN algorithm. The DNA sequences are translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. In some cases, the sequencing data from two or more clones containing overlapping segments of DNA are used to construct contiguous DNA sequences.

Sequence alignments and percent identity calculations can be performed using the Megalign program of the LASERGENE bioinformatics computing suite (DNASTAR Inc., Madison, Wis.). Multiple alignment of the sequences can be performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method are KTUPLE 1, GAP PENALTY= 3, WINDOW=5 and DIAGONALS SAVED=5.

The proteinase inhibitor-like sequence of SEQ ID NO:2 has 39% sequence identity from about a.a. 22–62 and 62% sequence identity from about a.a. 87–94 to a Bowman-Birk type proteinase inhibitor DE-4 (Accession No. P01059); 44% sequence identity from about a.a. 25–49, about 40% identity from about a.a. 36–50, and about 44% identity from about a.a. 54–62 to a Bowman-Birk type proteinase inhibitor (MSTI) (Accession No. P80321).

Example 4
Transformation and Regeneration of Transgenic Plants

Immature maize embryos from greenhouse donor plants are bombarded with a plasmid containing the proteinase inhibitor-like sequences of the present invention operably linked to a ubiquitin promoter and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

This plasmid DNA plus plasmid DNA containing a PAT selectable marker is precipitated onto 1.1 $\mu$m (average diameter) tungsten pellets using a $CaCl_2$ precipitation procedure as follows:

100 $\mu$l prepared tungsten particles in water
10 $\mu$l (1 $\mu$g) DNA in Tris EDTA buffer (1 $\mu$g total DNA)
100 $\mu$l 2.5 M $CaCl_2$
10 $\mu$l 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 $\mu$l 100% ethanol is added to the final tungsten particle pellet. For particle gun bombardment, the tungsten/DNA particles are briefly sonicated and 10 $\mu$l spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for and altered level of expression of the proteinase inhibitor-like sequence of the invention. Alternatively, the proteinase inhibitor-like activity can be assayed (i.e., enhance disease resistance).

Bombardment and Culture Media

Bombardment medium (560Y) comprises 4.0 g/l N6 basal salts (SIGMA C-1416), 1.0 ml/l Eriksson's Vitamin Mix (1000X SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 $\mu$l N6 basal salts (SIGMA C-1416), 1.0 ml/l Eriksson's Vitamin Mix (1000X SIGMA-1511), 0.5 mg/l thiamine HCl, 30.0 $\mu$l sucrose, and 2.0 mg/l 2,4-D (brought to volume with D-I $H_2O$ following adjustment to pH 5.8 with KOH); 3.0 $\mu$l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117–074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117–074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 µl bacto-agar (added after bringing to volume with polished D-I $H_2O$), sterilized and cooled to 60° C.

Example 5
Agrobacterium-mediated Transformation

For Agrobacterium-mediated transformation of maize with a proteinase inhibitor-like preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the defense-inducible nucleotide sequences to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 6
Soybean Embryo Transformation

Soybean embryos are bombarded with a plasmid containing the proteinase inhibitor-like sequence operably linked to an Scp1 promoter (U.S. Pat. No. 6,072,050) as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the proteinase inhibitor-like sequence operably linked to the Scp1 promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7
Sunflower Meristem Tissue Transformation

Sunflower meristem tissues are transformed with an expression cassette containing the proteinase inhibitor-like sequence operably linked to an Scp1 promoter as follows (see also European Patent Number EP 0 486233, herein incorporated by reference, and Malone-Schoneberg et al.

(1994) *Plant Science* 103:199–207). Mature sunflower seed (*Helianthus annvus* L.) are dehulled using a single wheathead thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9:55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA$_3$), pH 5.6, and 8 g/l Phytagar.

The explants are subjected to microprojectile bombardment prior to Agrobacterium treatment (Bidney et al. (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® (particle acceleration device.

Disarmed *Agrobacterium tumefaciens* strain EHA105 is used in all transformation experiments. A binary plasmid vector comprising the expression cassette described above is introduced into Agrobacterium strain EHA105 via freeze-thawing as described by Holsters et al. (1978) *Mol. Gen. Genet.* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an OD$_{600}$ of about 0.4 to 0.8. The Agrobacterium cells are pelleted and resuspended at a final OD$_{600}$ of 0.5 in an inoculation medium comprised of 12.5 mM MES pH 5.7, 1 gm/l NH$_4$Cl, and 0.3 gm/l MgSO$_4$.

Freshly bombarded explants are placed in an Agrobacterium suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for the activity of the defense inducible sequences.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of T$_0$ plants (parental generation) maturing in the greenhouse are identified by NPTII ELISA and/or by the analysis of the activity of the defense induced sequences in the leaf extracts while transgenic seeds harvested from NPTII-positive T$_0$ plants are identified by the analysis of the activity the defense induced sequences in small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into Agrobacterium tumefaciens strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l NH$_4$Cl and 0.3 g/l MgSO$_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP. IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for defense induced activity using assays known in the art. After positive (i.e., for defense-inducible expression) explants are identified, these shoots that fail to exhibit defense-inducible activity are discarded, and every positive explant is subdivided into nodal explants. One nodal explant contains at least one potential node. The nodal segments are cultured on GBA medium for three to four days to promote the formation of auxiliary buds from each node, Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for defense-inducible expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 8
Anti-fungal and Anti-bacterial Assays

The anti-fungal and anti-bacterial activity of the proteinase inhibitor-like polypeptide of the invention can be tested using a variety of assays. The proteinase inhibitor-like polypeptide is expressed and isolated using routine methods, such as the Rapid Translation System produced by Roche. The polypeptide is then tested for activity.

Anti-fungal Assays: *F. graminearum* is grown in half-strength CM-cellulose-yeast extract broth (7.5 g of CM-cellulose, 0.5 g of yeast extract, 0.25 g of $MgSO_4.7H_2O$, 0.5 g of $NH_4NO_3$, and 0.5 g of $KH_2PO_4$ per liter of distilled water). Cultures are shaken at 200 rpm at 28° C. in the light. After 7 days, cultures are filtered through two layers of sterile cheesecloth and the resulting filtrate is passed through a Nalgene 0.45-μm disposable filter unit. Conidia (spores) are collected on the membrane, washed with sterile distilled water, and resuspended in a small volume of sterile water. Conidia are counted with a hemocytometer and stored at 4° C. for not longer than 1 month. *A. longipes* cultures are grown on carrot agar at 28° C. under continuous fluorescent light, and *F. moniliforme* and *A. flavus* are grown on oatmeal agar at 28° C. under ambient light. For these three fungi, conidia are collected by scraping a sterile inoculating loop across the surface of the plate. Concentrated suspensions are made in sterile water with 0.1% Tween 20. Conidia are counted with a hemocytometer and used immediately. For an assay, fungal spore suspensions are diluted to give a concentration of 250 spores/90 μl of dilute culture medium (0.037 g of NaCl, 0.0625 g of $MgSO_4.7H_2O$, 0.25 g of calcium nitrate, 2.5 g of glucose, 0.25 g of yeast extract, 0.125 g of casein hydrolysate (enzyme), and 0.125 g of casein hydrolysate (acid) in 7.5 mm sodium phosphate buffer, pH 5.8).

For Sclerotinia cultures, mycelia are grown on cellophane discs (52 mm) overlain on V8 agar. When hyphal growth reaches the margin of the disc, the cellophane is removed and the mycelium is dislodged by vortexing in 10 ml of diluted culture medium, followed by filtration through two layers of cheesecloth. Hyphal pieces are washed by centrifugation at 2000 rpm for 5 min anl are resuspended in diluted growth medium to give a concentration of approximately 50 hyphal pieces/90 μl.

To perform anti-fungal assays, 10 μl of test material in water or 0.01% acetic acid are added to wells of a microtiter plate. Ninety microliters of spores or hyphal pieces are added and mixed. Plates are covered and incubated at 28° in the dark for 24–48 h. Growth is evaluated visually using an inverted microscope, and a scale of 0–4 is used to rate the effect of added peptide (0=no observable inhibition relative to water control; 1=slight inhibition; 2=substantial inhibition; 3=almost complete inhibition; 4=complete inhibition).

Anti-bacterial Assays. Cultures are grown to midlog phase (*E. coli* in LB broth and *C. nebraskense* in NBY) and are then harvested by centrifugation (2000×g for 10 min). Cells are washed with 10 mM sodium phosphate buffer, pH 5.8 (*C. nebraskense*) or pH 6.5 (*E. coli*) by centrifugation and then colony forming units are estimated spectrophotometrically at 600 nm with previously established colony forming unit-optical density relationships used as a reference.

Assays for bactericidal activity are performed by incubating $10^5$ bacterial colony forming units in 90 $\mu$l with 10 ml of peptide (or water for control). After 60 min at 37° C. (*E. coli*) or 25° C. (*C. nebraskense*), four serial, 10-fold dilutions are made in sterile phosphate buffer. Aliquots of 100 $\mu$l are plated on LB or NBY plates, using 1 or 2 plates/dilution. Resulting colonies are counted, and the effect of the peptide is expressed as percent of initial colony count (Selsted et al. (1984) *Infect. Immun.* 45:150–154).

Assays for bacteriostatic activity are performed by incubating $10^5$ bacteria with MBP-1 in 200 $\mu$l of dilute medium (1 part NBY broth to 4 parts 10 mM sodium phosphate, pH 5.8) in microtiter plate wells. Plates are covered, sealed, and incubated at 28° C. Growth is monitored spectrophotometrically at 600 nm. After 41 h controls will have grown sufficiently (optical density >0.20) to measure effect of peptide as percent of control.

Example 9

Protease Inhibition Assays

Apparent $K_i$ values are determined for the wild type proteinase inhibitor-like sequences of the invention using the equation $V_o/V_i=1+[I]/K_{i(app)}$, where $V_o$ is the reaction rate in the absence of inhibitor, and $V_i$ is the reaction rate in the presence of inhibitor (Nicklin and Barrett (1984) *Biochem J.* 223:245–249). Reactions without inhibitor are started by addition of substrate, and the linear increase in absorbance at 405 nm is monitored over time and the reaction rate calculated from the slope. A known quantity of inhibitor is then added to the same reaction, and the new reaction rate is determined. The following proteases can be used: bovine pancreatic chymotrypsin, bovine pancreatic trypsin, porcine pancreatic elastase and subtilisin Carlsberg from *Bacillus licheniformis* (all from Sigma). Assays are done at 37° C. for chymotrypsin, and at 25° C. for the other proteases. Reaction volumes are typically 200 $\mu$l. The following substrates are used at a concentration of 1 mM: N-succinyl-Ala-Ala-Pro-Phe-p-nitronalide (Sigma) for chymotrypsin and subtilisin, N-benzoyl-2-Ile-Glu-Gly-Arg-p-nitroanilide (Chromogenix S-2222) for trypsin and N-succinyl-Ala-Ala-Ala-p-nitroanilide (Sigma) for elastase. Chymotrypsin, elastase and subtilisin assays are done in 200 mM Tris-HCl, pH 8.0, with 1 $\mu$M bovine serum albumin included. Trypsin assays are done in 50 mM Tris-HCl, 2 mM NaCl, 2 mM CaCl$_2$, 0.005% TritonX-100, pH 7.5.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleotide sequence comprising the sequence set forth in SEQ ID NO:3.

2. A DNA construct comprising a promoter having the nuclcotide sequence of claim 1 operably linked to a nucleotide sequence of interest.

3. An expression vector comprising the DNA construct of claim 2.

4. A plant having stably incorporated into its genome at least one DNA construct comprising a nucleotide sequence of interest operably linked to a promoter, wherein said nucleotide sequence of interest is heterologous to said promoter and wherein said promoter comprises the sequence set forth in SEQ ID NO:3.

5. A plant cell comprising the vector of claim 3.

6. A method of regulating the expression of a nucleotide sequence of interest, said method comprising stably incorporating in the genome of a plant cell a nucleotide sequence of interest operably linked to a promoter comprising the nucleotide sequence of claim 1, wherein said nucleotide sequence of interest is heterologous to said promoter.

7. The method of claim 6, further comprising contacting said plant cell with a stimulus that induces expression of said nucleotide sequence of interest.

* * * * *

SEQUENCE LISTING

```
<160> NUMBER OF SEQ ID NOS: 4

<210> SEQ ID NO 1
<211> LENGTH: 565
<212> TYPE: DNA
<213> ORGANISM: Zea mays
<220> FEATURE:
<221> NAME/KEY: misc_feature
<222> LOCATION: (0)...(0)
<223> OTHER INFORMATION: Proteinase Inhibitor-Like cDNA
<220> FEATURE:
<221> NAME/KEY: CDS
<222> LOCATION: (60)...(353)

<400> SEQUENCE: 1
gacccacgcg tccgctggcc tgttcttaat tattgccagg acaggagaaa caaacaaag        59 atg agg cct cag ctg ata ctc gtc ggc act ctg gct gtt ctc gcc atc      107
Met Arg Pro Gln Leu Ile Leu Val Gly Thr Leu Ala Val Leu Ala Ile
 1               5                  10                  15 ctc gca gct ctc ggc gaa ggc tcg tcg tcc tgg ccg tgc tgc aac aac      155
Leu Ala Ala Leu Gly Glu Gly Ser Ser Ser Trp Pro Cys Cys Asn Asn
                20                  25                  30 tgc ggt gct tgc aac agg aag cag ccg cct gag tgc cag tgc aat gac      203
Cys Gly Ala Cys Asn Arg Lys Gln Pro Pro Glu Cys Gln Cys Asn Asp
            35                  40                  45 gtg tcg gtg aac ggg tgc cat ccg gag tgc atg aac tgc gtc aag gtc      251
Val Ser Val Asn Gly Cys His Pro Glu Cys Met Asn Cys Val Lys Val
        50                  55                  60 ggt gca gga att cgt ccc ggc atg ggc ccc ggc ccc gtc gtc acc tac      299
Gly Ala Gly Ile Arg Pro Gly Met Gly Pro Gly Pro Val Val Thr Tyr
 65                  70                  75                  80 cgc tgt gat gac gtt ctc aca aac ttc tgc cag agc agc tgc ccg gag      347
Arg Cys Asp Asp Val Leu Thr Asn Phe Cys Gln Ser Ser Cys Pro Glu
                85                  90                  95 gcg tag ttgctgggtg gtggtgtctt cttctgacgc catgggacgc cagtacgcaa        403
Ala * ccagtttgct tctctccagc ttcgtcagac aagaaataga taaataaaca aatgtcaccg      463
gccgctctgt tcggtgcttg ctcttgttcg tcgtcagaga agaaatagat aaataaataa      523
ataaataaat aaatagccaa aaaaaaaaaa aaaaaaaaa aa                          565

<210> SEQ ID NO 2
<211> LENGTH: 97
<212> TYPE: PRT
<213> ORGANISM: Zea mays

<400> SEQUENCE: 2

Met Arg Pro Gln Leu Ile Leu Val Gly Thr Leu Ala Val Leu Ala Ile
 1               5                  10                  15

Leu Ala Ala Leu Gly Glu Gly Ser Ser Ser Trp Pro Cys Cys Asn Asn
                20                  25                  30

Cys Gly Ala Cys Asn Arg Lys Gln Pro Pro Glu Cys Gln Cys Asn Asp
```

```
                35                  40                  45
         Val Ser Val Asn Gly Cys His Pro Glu Cys Met Asn Cys Val Lys Val
             50                  55                  60

Gly Ala Gly Ile Arg Pro Gly Met Gly Pro Gly Pro Val Val Thr Tyr
         65                  70                  75                  80

Arg Cys Asp Asp Val Leu Thr Asn Phe Cys Gln Ser Ser Cys Pro Glu
                         85                  90                  95

Ala

<210> SEQ ID NO 3
<211> LENGTH: 925
<212> TYPE: DNA
<213> ORGANISM: Zea mays
<220> FEATURE:
<221> NAME/KEY: misc_feature
<222> LOCATION: (0)...(0)
<223> OTHER INFORMATION: Proteinase Inhibitor-like promoter

<400> SEQUENCE: 3
actatagggc acgcgtggtc gacggcccgg gctggtcgta tttgtgtcca acatttttga      60
tgtgatgggt cagcccctta tacgattgcc ttacgttatg aatggctata atattggaaa     120
cgacatcagc agtggaagtc gctggtcgtt gggttgcagc gtgtatacgt ggcatctagg     180
tggccttgat tttcttcttt gtcgcactgt ttctacattt cattggcaga tatgtatgaa     240
ctaaattatt ggccacttaa ggaggtgttt gaatgcaata aaactaatag ttagttggct     300
aaaattgtta gtgaaattat ctagctaaca aatagctacc taactattaa ctaatttacc     360
aaaaataact tatagttaaa ttattaagtt gggctgtttg aatgtctcaa ctaattttag     420
ccactaactt ttatctttag tgcattcaaa catggcataa gtctacgttt gatttgagac     480
ggtagcatcg tgcgtacgga agaggaacca aaaggatttt ccttgaaaat tttcatgcac     540
gtgggccgcc tgcagacgga gatgagcacc gcgaaatcaa tctggataga tcgtcgtctc     600
gtcaatcatt gcggtgctga cggtctaatt ttcctgcaac cagcaacttg aaagagacag     660
tctaggagga ttgtcaaaaa tatataatgc ttggcttcta cgtacgtacc tgttggccct     720
ggtggtcaaa gatgatcttc aagaaaacat cctggatttt cctctttcat atattcatat     780
tcaccgtcag tacgcgtgta tgatttggct ttgtatttgc ttcttgtaca agagatgaac     840
gaaagtgcaa ggaagcctcc ctcgatcccc tcctctatat atatatatac aagaagacct     900
tagagccgca ggaaggaaat ctatc                                           925

<210> SEQ ID NO 4
<211> LENGTH: 72
<212> TYPE: DNA
<213> ORGANISM: Artificial Sequence
<220> FEATURE:
<223> OTHER INFORMATION: oligonucleotide primer

<400> SEQUENCE: 4
ggccgctcga gtccaaagtc aggtcacagt gacctgatca aagttgtcca agtcaggtc      60 acagtgacct ga                                                         72
```